US012673184B2

(12) United States Patent
Shah et al.

(10) Patent No.: US 12,673,184 B2
(45) Date of Patent: Jul. 7, 2026

(54) ACCESS DEVICE

(71) Applicant: InnoVital, LLC, Beltsville, MD (US)

(72) Inventors: Amit Navin Shah, North Potomac, MD (US); Curt Steven Kothera, Rockville, MD (US); Pablo Javier Sztein, Silver Spring, MD (US); Gregory John Hiemenz, Silver Spring, MD (US)

(73) Assignee: InnoVital, LLC, Calverton, MD (US)

( * ) Notice: Subject to any disclaimer, the term of this patent is extended or adjusted under 35 U.S.C. 154(b) by 27 days.

(21) Appl. No.: 18/388,194

(22) Filed: Nov. 9, 2023

(65) Prior Publication Data

US 2024/0189549 A1 Jun. 13, 2024

Related U.S. Application Data

(63) Continuation of application No. PCT/US2022/028584, filed on May 10, 2022, which is a continuation of application No. 16/040,104, filed on Jul. 19, 2018, now Pat. No. 11,351,343, which is a continuation-in-part of application No. 15/612,707, filed on Jun. 2, 2017, now abandoned.

(60) Provisional application No. 63/256,339, filed on Oct. 15, 2021, provisional application No. 63/186,370, filed on May 10, 2021.

(51) Int. Cl.
*A61M 25/06* (2006.01)
*A61M 25/01* (2006.01)

(52) U.S. Cl.
CPC .... *A61M 25/0606* (2013.01); *A61M 25/0113* (2013.01); *A61M 25/0625* (2013.01); *A61M 25/0631* (2013.01); *A61M 2202/0007* (2013.01)

(58) Field of Classification Search
CPC .......... A61M 25/0606; A61M 25/0113; A61M 25/0625; A61M 25/0631; A61M 2202/0007; A61M 2005/1585; A61M 25/06; A61M 25/0612; A61M 25/0618; A61M 25/0655; A61M 25/01; A61M 25/0643
See application file for complete search history.

(56) References Cited

U.S. PATENT DOCUMENTS

| | | | |
|---|---|---|---|
| 3,536,073 A | 10/1970 | Farb | |
| 4,108,175 A | 8/1978 | Orton | |
| 4,747,831 A | 5/1988 | Kulli | |
| 4,781,692 A | 11/1988 | Jagger et al. | |

(Continued)

FOREIGN PATENT DOCUMENTS

WO WO-9857689 A1 * 12/1998 ........ A61M 25/0625

*Primary Examiner* — Lauren P Farrar
*Assistant Examiner* — Leah J Swanson
(74) *Attorney, Agent, or Firm* — Royal Craig, LLC; Royal W. Craig

(57) ABSTRACT

The present invention is a simple-to-use access device with a safety feature. A catheter advancer (30) is slidably and rotatably integrated with a base (10) to guide advancement of a catheter (50) linearly along the insertion path of a needle (60) and catheter (50). The catheter advancer (30) engages the base (10), catheter (50) and needle (60) and both sequences and delimits relative movement between the base (10), catheter advancer (30), catheter assembly (50) and needle (60). The access device stabilizes and guides the critical needle insertion and catheter advancement steps of a complication-prone and very common procedure.

19 Claims, 8 Drawing Sheets

(56)                    References Cited

U.S. PATENT DOCUMENTS

| | | | |
|---|---|---|---|
| 4,832,696 A | | 5/1989 | Luther et al. |
| 5,137,517 A | | 8/1992 | Loney et al. |
| 5,186,712 A | * | 2/1993 | Kelso ................ A61M 25/0606 604/177 |
| 5,250,036 A | * | 10/1993 | Farivar ............. A61M 25/0643 604/164.01 |
| 5,279,590 A | | 1/1994 | Sinko |
| 5,700,250 A | | 12/1997 | Erskine |
| 6,126,633 A | | 10/2000 | Kaji et al. |
| 6,273,871 B1 | | 8/2001 | Davis et al. |
| 6,620,136 B1 | | 9/2003 | Pressly, Sr. et al. |
| 9,744,344 B1 | | 8/2017 | Devgon et al. |
| 9,839,768 B2 | | 12/2017 | Ibragimov |
| 2004/0087913 A1 | * | 5/2004 | Rogers .............. A61M 25/0631 604/263 |
| 2011/0224617 A1 | * | 9/2011 | Miner ............... A61M 25/0631 604/164.08 |
| 2015/0305769 A1 | * | 10/2015 | Ibragimov ........ A61M 25/0606 606/180 |
| 2016/0361089 A1 | * | 12/2016 | Farley ............... A61M 25/0631 |
| 2017/0120014 A1 | | 5/2017 | Harding et al. |
| 2018/0344985 A1 | * | 12/2018 | Shah ................. A61M 25/0606 |

* cited by examiner

ACCESS DEVICE

CROSS-REFERENCE TO RELATED APPLICATIONS

The present application is a continuation of PCT/US22/28584 filed May 10, 2022, which in turn was a continuation of U.S. patent application Ser. No. 16/040,104 filed on 19 Jul. 2018 (now U.S. Pat. No. 11,351,343).

STATEMENT REGARDING FEDERALLY SPONSORED RESEARCH

This invention was made with U.S. Government support under Contract No. W81XWH-18-C-0068, awarded by USAMRAA. The U.S. Government has certain rights in this invention.

BACKGROUND OF THE INVENTION

Technical Field

The present invention relates to medical devices and, more particularly, a device for accessing a body cavity, blood vessel, or any other natural or potential space, duct, or path within the body either with or without image guidance.

Accessing a blood vessel or body cavity for the purposes of infusion, medication or device delivery, drainage, monitoring, or other purpose commonly involves the initial use of a puncturing needle. The needle penetrates the tissue that lies superficial to the space of interest and may be used to deliver a catheter, probe, or guidewire into the space of interest. Commonly encountered complications of this approach—even when image guidance is employed—are (a) injury to nearby tissues from the needle tip often due to unintended needle micromotion and (b) lack of control of the movement of components relative to one another. For example, lack of control of an overlying catheter and/or of the sliding movement of the catheter and needle relative to one another may lead to injury, failure of the procedure, and damage to the components themselves. A device that decreases the likelihood of injury from the needle tip by effectively removing, reorienting, or shielding the sharp bevel after it has served its function of accessing the body cavity of interest and/or that enhances user control over specific components that ordinarily move in a less restricted fashion would prove useful in enhancing procedural success and decreasing procedural complications. Device components, features, and movements may be visible with image guidance.

As an example procedure, venous access is among the critical first steps in patient care allowing fluids, blood products, and medications to be quickly and reliably administered. Accordingly, 60-90% of hospitalized patients require a peripheral IV during their hospital stay. Over 300 million peripheral IV's are sold yearly in the US and over 1 billion units are sold worldwide. However, in 12-26% of adult patients and 24-54% of pediatric patients, the first attempt at catheter insertion fails, requiring additional, painful attempts. Moreover, blood vessel trauma resulting from failed insertion attempts increases the risk of subsequent catheter failure, with failure defined as catheter removal before the end of its intended dwell time or before the CDC recommended 72-96 hour dwell time limit. Peripheral IV's fail at a rate of 35-50% due to painful processes such as inflammation (phlebitis); fluid or medication leakage into surrounding tissue (infiltration); dislodgment; mechanical failure (e.g., occlusion); and site or bloodstream infection. Unsuccessful IV insertion attempts and IV failures are expensive in terms of direct equipment costs; provider time; necessitating more invasive venous access procedures; management of complications; additional hospital days; and, of course, the patient's pain and dissatisfaction.

Providers with high levels of training and experience have a significantly higher first pass success rate and lower incidence of ultimate IV failure, both of which directly reduce the pain experienced by the patient. Of course, training and experience are, by their very nature, time-intensive and otherwise expensive to acquire. An innovative device that enables novices to mimic a fluid expert approach could be of great value, provided that it is rigorously designed to meet patient, disease process, user, environmental, size, weight, and cost requirements.

The past several years has seen innovation relevant to IV placement. Examples include ultrasound and near-infrared technologies to aid vessel identification; antibiotic-impregnated and other cleansing approaches to tubing, connectors and dressings; and novel approaches to catheter stabilization. However, little has been done to simplify the often-difficult task of actual IV insertion. In fact, novel technologies often assume a baseline level of competency with IV placement—an assumption that is not supported by the literature cited above, nor recent reports of >20% nursing turnover and high nursing vacancy rates in emergency settings. Emergency Medical Services (EMS) providers also turn over frequently. Functionally, high turnover rates in emergency settings equate to less experienced providers attempting IV placement on patients who are often the most difficult to access (e.g., due to dehydration) and in the most immediate need. Again, a device that simplifies the most difficult aspects of IV insertion could be of value.

Several of the steps followed for IV insertion require precision and a steady hand to prevent the needle from going all the way through the vein. Senior nurses, and the literature, counsel new nurses to pay special attention to these steps, especially in patients who have difficult-to-access veins due to dehydration, excess or thin skin, scarring, obesity, and edema, among other conditions. As described in primers on IV placement written by nurse educators, the most common errors after appropriate target vessel identification and tourniquet placement are related to vein stabilization, angle of approach, and IV assembly advancement after a flash of blood is visualized, offering an opportunity for innovation.

Regarding related art, U.S. Pat. No. 4,832,696 to Luther et al. issued May 23, 1989, shows an assembly designed to permit the insertion of an "over-the-needle" catheter. U.S. Pat. No. 9,744,344 to Devgon et al. issued Aug. 29, 2017 shows a catheter introducer which, as shown in FIGS. 12-14, includes a set of ribs 436 distributed along at least a portion of the introducer 410 which vibrate the device to provide the user with a haptic, tactile, and/or audible indicator associated with a position of the catheter 460 relative to the introducer 410. U.S. Pat. No. 4,108,175 to Orton issued 22 Aug. 1978 shows a catheter insertion device that can be controlled entirely by one hand and which has a flash chamber.

U.S. Pat. No. 6,620,136 to Pressly, Sr. et al. issued Sep. 16, 2003 shows a retractable I-V catheter placement device with a magnified transparent verification cavity in the needle hub for viewing blood flash.

U.S. Pat. No. 3,536,073 to Farb discloses an enlarged needle having a bore of sufficient diameter to accommodate a catheter. The needle is secured to a plunger which is slidably mounted within housing. A tubular protective sheath is disposed intermediate the needle and the housing and the protective tubing can be advanced to surround the needle after it is withdrawn from the patient's body.

U.S. Pat. No. 4,781,692 to Jagger, et al. discloses a protective arrangement for a catheter insertion needle wherein the needle is pulled into a protective position within a surrounding tube by a pulling force applied through a flexible tube.

U.S. Pat. No. 5,279,590 to George E. Sinko et al. issued 19 Jan. 1994 shows a tubular catheter placement guide. After the catheter is advanced, the needle can be retracted into a housing and locked into place with a tab 20.

United States Patent Application 20170120014 by Harding et al. published May 4, 2017 shows an intravenous catheter securement platform with a textured paddle grip.

U.S. Pat. No. 5,700,250 to Erskine issued Dec. 23, 1997 shows a catheter-advancement system with a hollow barrel that houses a needle hub. A movable latch initially maintains the needle hub adjacent to the distal end of the barrel and then enables retraction of the needle into the barrel.

U.S. Pat. No. 5,137,517 Loney et al. issued Aug. 11, 1992 shows an advancer for catheters or guidewires with a body having a longitudinal slot that fits a slidable insert. Moving the insert longitudinally relative to the body activates a slide arrangement.

U.S. Pat. No. 6,273,871 to Davis et al. issued Aug. 14, 2001 shows a splittable catheter introducer having a pair of wings and an introducer needle.

U.S. Pat. No. 6,126,633 to Kaji et al. issued Oct. 3, 2000 shows a needle applicator with markers 5 as indexes for the depth of insertion, which are arranged at regular intervals in the axial direction. Preferably, each interval ranges from 3 to 5 mm.

U.S. Pat. No. 4,747,831 to Kulli discloses a needle operating assemblage which can be utilized for insertion of a cannula or over-the-needle catheter wherein the positioning of the needle in its operative opposition compresses a spring between a shoulder provided on the outer end of the needle and a latch mounted for radial movement relative to the housing. After the venipuncture is accomplished, depressing the latch permits the needle to be retracted by the spring to a position where in the pointed end of the needle lies within the end of the housing.

U.S. Pat. No. 9,839,768 by Ibragimov shows an introducer catheter wherein the needle hub includes an actuator configured to rotate the needle by about half of a turn What follows is a description specific to a device for the venous access procedure designed to enhance safety and usability. One skilled in the art will appreciate the analogous anatomical structures, device components, component movement, and user actions for other access procedures and access devices which fall under the same invention.

SUMMARY OF THE INVENTION

Technical Problem

Accessing a blood vessel or body cavity for the purposes of infusion, medication or device delivery, drainage, monitoring, or other purpose requires appropriate target vessel identification, vein stabilization, angle of approach, orientation, and IV assembly advancement after a flash of blood is visualized, all requiring precision and a steady hand to prevent the needle from going all the way through the vein.

It is, therefore, an object of the present invention to provide an easy-to-use access device that is designed to enhance procedural safety and success as well as usability.

It is another object to precisely control initial advancement of the catheter tip, prior to threading the catheter into the vessel, to just beyond the distal needle tip to a predetermined length that is just enough to fully sheath the bevel of the needle tip, without overextension, to avoid risk of shearing/cutting.

It is an overarching object to provide an access device with the foregoing qualities that, for the exemplary IV device, facilitates a higher first attempt placement success rate and decreased vessel trauma and, as a result, decreased IV failures, increased patient comfort and satisfaction, and decreased cost.

Solution to Problem

In accordance with the foregoing objects, the invention disclosed herein is a simple-to-use IV device with a base, which is configured to be held by the user, a needle mounted in the base and extending distally therefrom with a sharp incising end, a catheter assembly comprising a distal catheter and proximal hub, which slides over the needle and interfaces with the distal end of the catheter advancer, and a catheter advancer slidably and rotatably integrated with the base and that engages and initiates one or more operational safety features. The catheter advancer simultaneously enables the following safety features for the exemplary IV device: (1) advances the catheter tip just beyond the needle tip to "sheath" the needle tip for safety, (2) rotates the point of the needle away from the back-wall of the vessel (bevel no longer facing up), (3) unlocks the catheter from the needle to enable catheter advancement relative to the needle (catheter is initially locked to avoid inadvertent catheter sliding relative to the needle and catheter shearing that may result), and (4) mechanically prevents the needle tip from being able to advance beyond the tip of the catheter. The initial advancement of the catheter tip to just beyond the needle tip is closely controlled to a predetermined length that is just enough to fully sheath the bevel of the needle tip, and yet not so far as to overextend, which risks shearing/cutting into the catheter. The initial advancement (1) is consistently limited to this pre-determined amount. After sheathing (1) and steps (2-4) are complete, the catheter may be advanced into the vessel manually by the user, as is common practice.

The foregoing components combine in an easy-to-use, handheld device that can stabilize and guide the critical needle insertion and catheter advancement steps of a complication-prone and very common procedure. The base serves as a stabilizing component that nests in the user's hand, designed to function as an extension of his/her fingers. The base provides a clear view of the flash chamber at the proximal end of the needle. The catheter advancer component slidably and rotatably integrates with the base component and may lock into place surrounding the needle after completion of the catheter advancement step of the IV insertion procedure. Engagement between the base and the catheter assembly prevents the catheter assembly from rotating relative to the catheter advancer during the rotation and initial advancement process, and yet the catheter advancer can be freely removed from the inserted catheter without any possibility of dislodging the catheter once it has been fully advanced.

The IV device enhances both safety and usability by facilitating small movements of the needle/catheter assembly or either part individually, such as with advancement of the catheter over the needle, all without interrupting the flow of the IV start procedure or reducing tactile feedback. The IV device also prevents unintended motion of the cannula or catheter relative to the needle.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

A device that decreases the likelihood of injury from the needle tip by effectively removing, reorienting, and/or shielding the sharp bevel after it has served its function of accessing the body cavity of interest and/or that enhances user control over specific components that ordinarily move in a less restricted fashion would prove useful in enhancing procedural success and decreasing procedural complications. Device components, features, and movements may be visible with image guidance. What follows is a description specific to a device for the venous access procedure. One skilled in the art will appreciate the analogous anatomical structures, device components, component movement, and user actions for other access procedures and access devices are within the scope and spirit of this invention.

One skilled in the art will appreciate that embodiments of the described approach may be used anytime a catheter is placed over a needle into a patient. As examples, the catheter may be placed into various blood vessels, body cavities, or airway structures. One skilled in the art will further recognize that the described approach has value even if a catheter is not delivered into the patient. Specifically, the advancement of a tubular, catheter-like structure just over the needle bevel once the needle is in position will shield surrounding tissues from unintended trauma from the needle tip.

Furthermore, one skilled in the art will appreciate that controlled catheter advancement may be performed in a semi-automated or fully automated manner. As an example, a needle or catheter placement device or system may include automated or semi-automated bevel sheathing via a triggered advancement of a catheter or catheter-like structure. In one embodiment, change in force exerted on the needle as the tip enters the body structure of interest may trigger catheter advancement. In another embodiment, flow of fluid (e.g., blood) into the needle or other device component may trigger catheter advancement. In such embodiments, the triggering action may affect the catheter advancement through traditional mechanical means such as, but not limited to, a lever, linkage, screw, gear, cam, or hydraulic mechanism. The triggering may also release stored mechanical energy to affect catheter advancement, such as but not limited to the release of a compressed spring.

The exemplary application of the present invention is an IV device to be placed without interrupting the flow of the typical IV start procedure.

Figure 1:
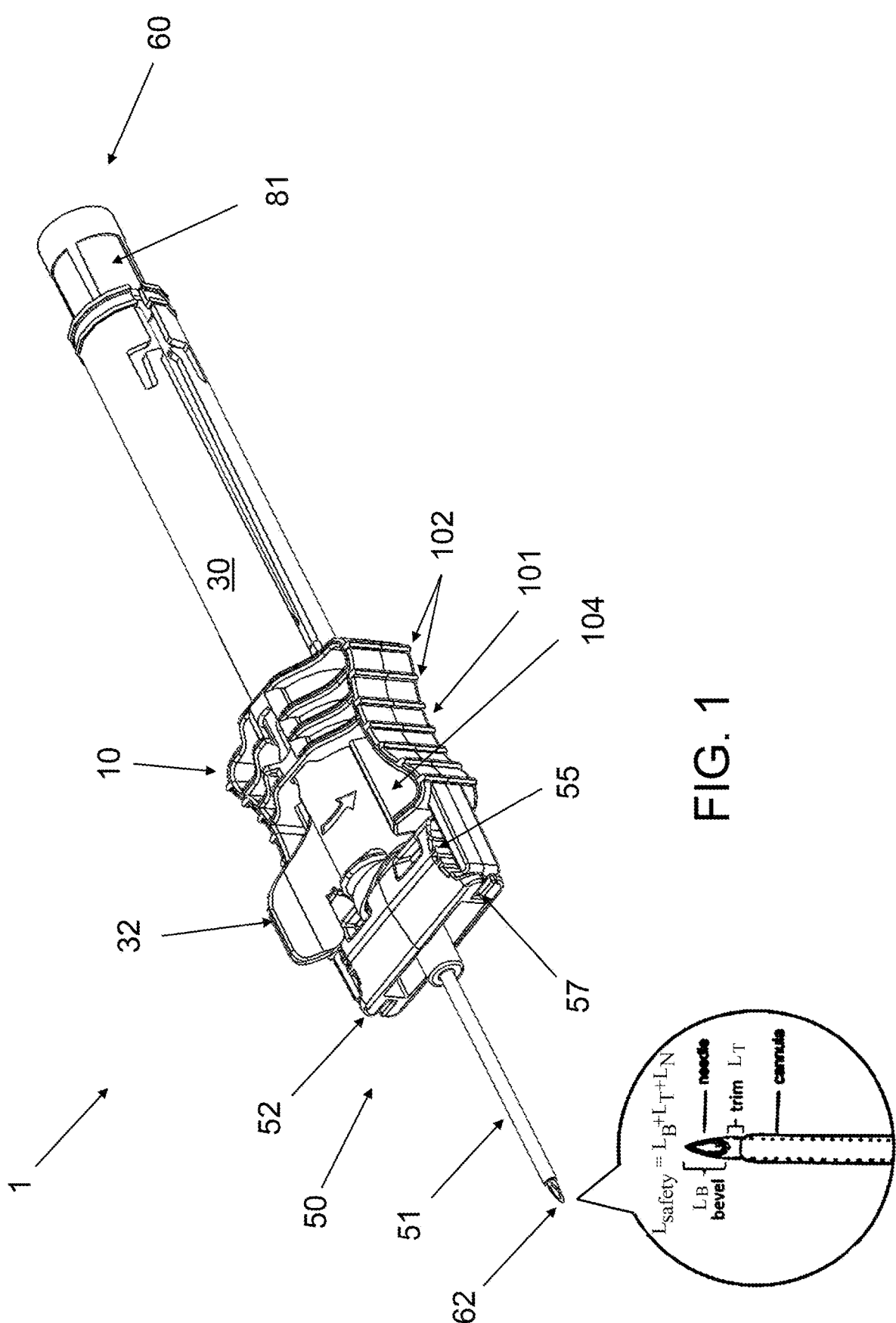
FIG. 1 is a perspective view of the intravenous device of the present invention.
Figure 2:
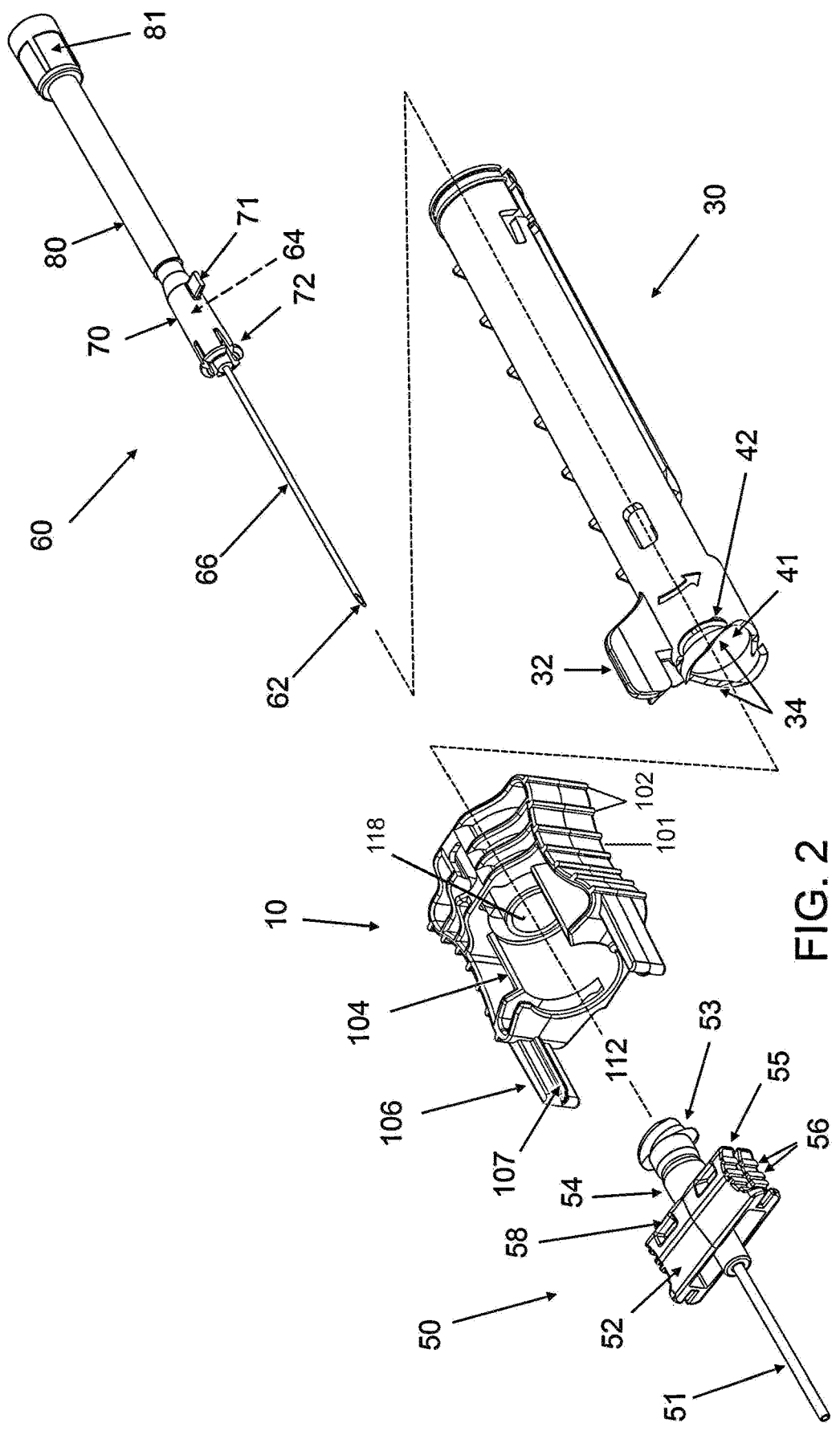
FIG. 2 is a perspective exploded illustration of the intravenous device of FIG. 1.
Figure 3:
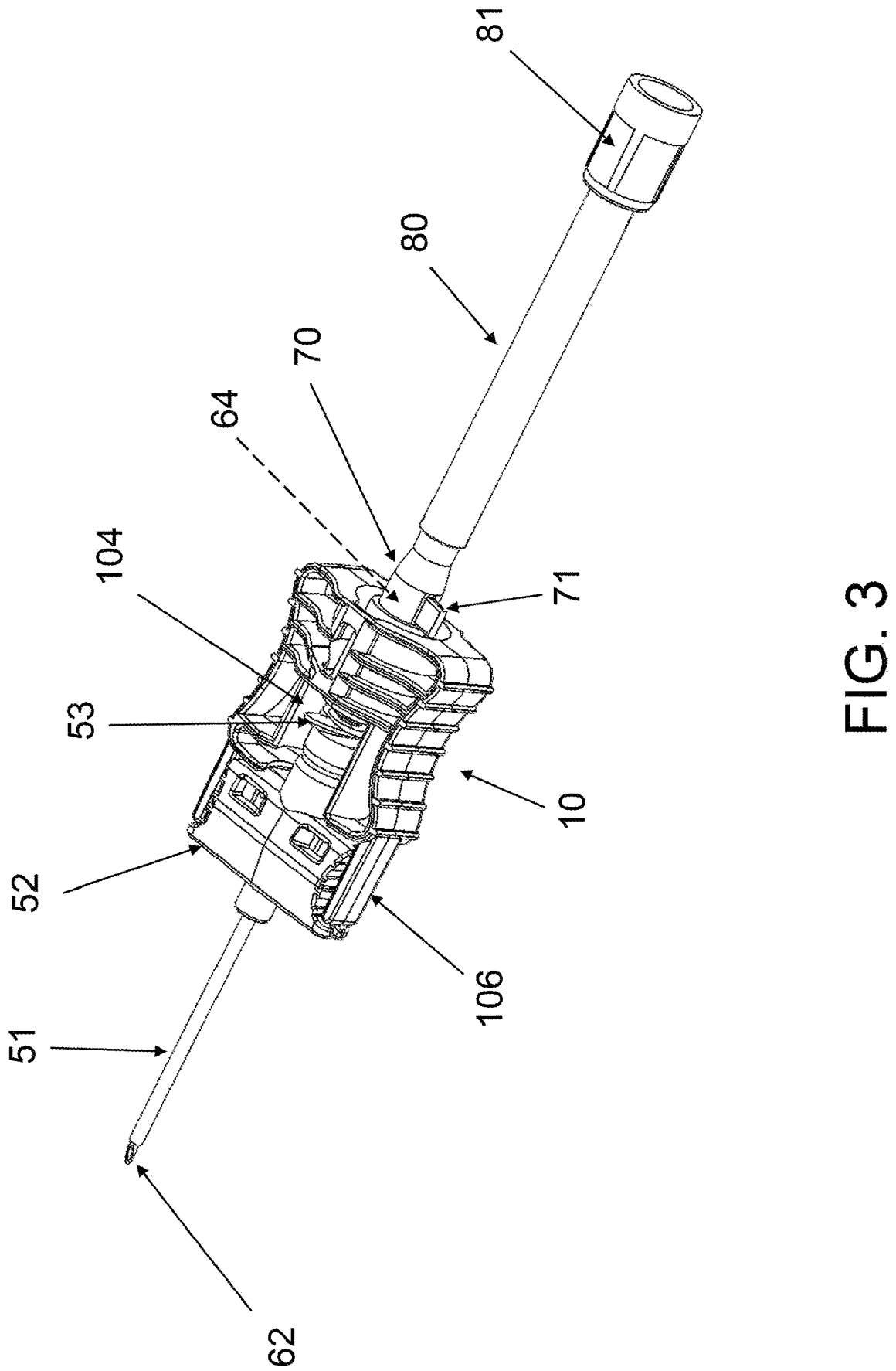
FIG. 3 is a rear perspective view of the intravenous device of FIG. 1 with the catheter advancer component removed.

With reference to FIGS. 1-3, the IV device 1 generally comprises a needle assembly 60 having a needle 66 with distally-beveled tip 62 and a proximal needle hub 70 that contains a flash chamber 64 for visualizing blood flashing back through the needle 66. In addition, a catheter assembly 50 comprises a distal catheter 51 and a proximal catheter hub 52. The IV device 1 also comprises a base 10, and a catheter advancer 30 slidably and rotatably journaled into base 10 and manually-actuated by a rotation tab 32 that protrudes generally radially therefrom, extending lengthwise along a center axis of the tubular structure of catheter advancer 30 and occupying a lengthwise span thereof. Base 10 preferably has sideward-contoured and gripped finger interfaces 101 oriented on the lateral faces of base 10 to allow a user to hold base 10 with a squeeze grip between the thumb and middle finger. Finger interfaces 101 preferably provide a wide grip such that the tips of the user's thumb and middle finger are spaced wide enough apart to clearly see between them, even for a gloved user with large fingers. To facilitate gripping, finger interfaces 101 are preferably concave and contain surface features for tactile feedback and control such as ribbed protrusions 102. Other patterned protrusions, indentions, and textures may also be used within the same invention.

The catheter hub 52 likewise preferably has sidewardly-gripped and contoured finger interfaces 55 oriented on the lateral faces of hub 52 such that the user can hold catheter assembly 50 with a squeeze grip between the thumb and middle/index finger. Finger interfaces 55 also preferably provide a wide grip such that the tips of the thumb and middle/index finger are spaced apart for a gloved user with large fingers for better control and security when attaching other devices/tubing to luer lock threads 53 on the proximal end. To facilitate gripping, finger interfaces 55 are preferably concave and contain surface features for tactile feedback and control such as ribbed protrusions 56.

Base 10 mechanically engages the other three primary subassemblies or components about common axis 112: catheter assembly 50, catheter advancer 30, and needle assembly 60. The needle hub 70 of needle assembly 60 engages with base 10 such that needle assembly 60/hub 70 can rotate about axis 112 through a defined angular range relative to base 10, but is constrained from relative translation along axis 112. Catheter hub 52 of catheter assembly 50 engages with base 10 such that catheter assembly 50/hub 52 can translate distally along axis 112, but is constrained from relative rotation about axis 112. Catheter advancer 30 engages with base 10 such that catheter advancer can rotate about axis 112 through a defined angular range relative to base 10, while being constrained from relative translation along axis 112, and then at a defined angular rotation becomes free to translate along axis 112. It is through these regulated rotational and translational engagements that the safety feature(s) of the present invention are activated as will be described.

Figures 6, 7:
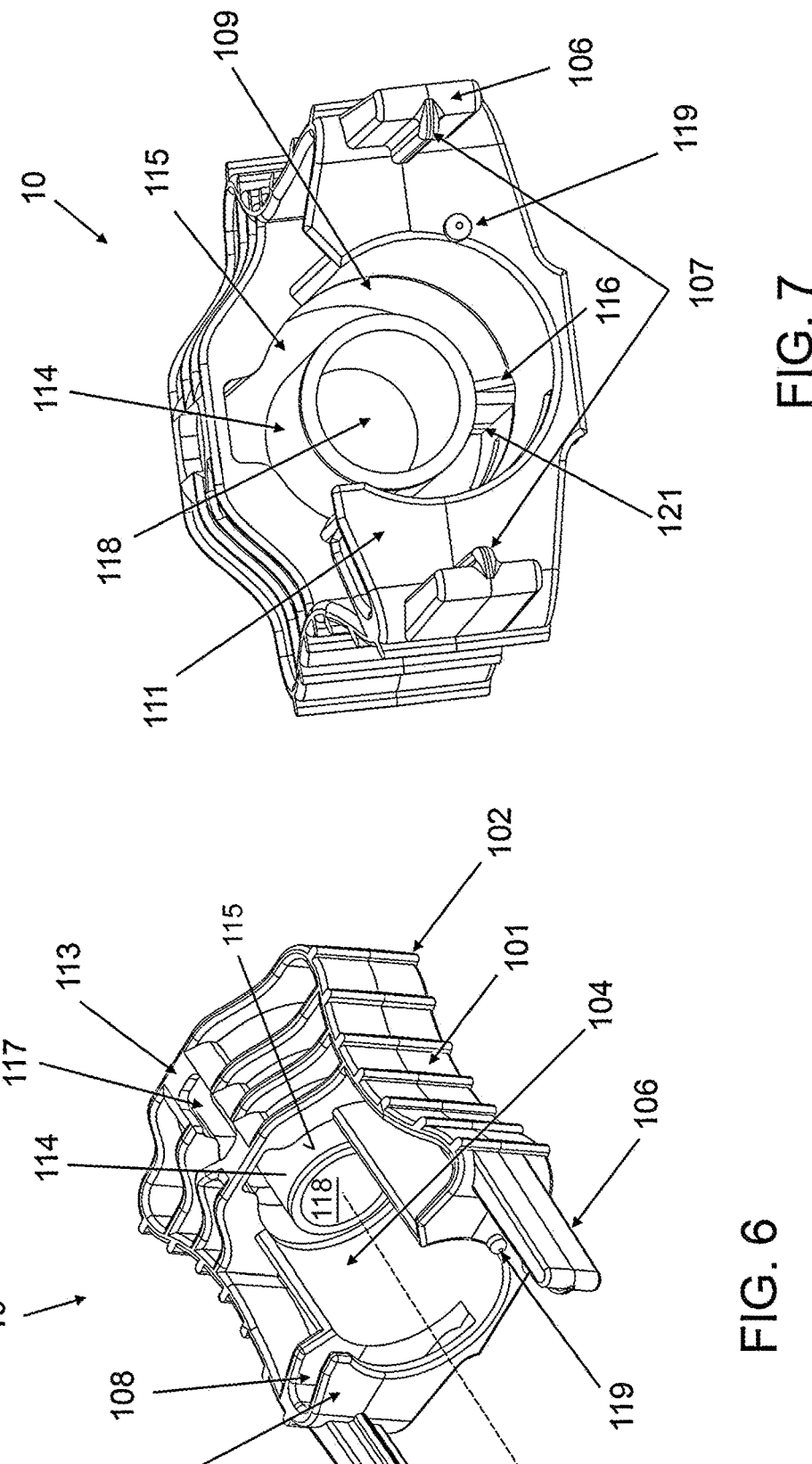
FIG. 6 is a top perspective view of the base 10 of FIGS. 1-3.
FIG. 7 is a front perspective view of the base 10 of FIGS. 1-3.

As seen in FIGS. 2, 6 and 7, base 10 is defined by a central cylindrical cavity 118 extending lengthwise end-to-end along axis 112 about which the other components selectively rotate and/or translate. Base 10 has a cylindrical collar 114 that defines inner cavity 118, wherein needle hub 70 (see FIG. 2) is seated for relative rotational movement. Collar 114 is aligned with axis 112, centrally supported by an elongate strut 116, and thereby holds needle assembly 60 centered about axis 112 via needle hub 70. External to cylindrical collar 114 is outer cavity 115 in which catheter advancer 30 is journaled for rotation and translation. Outer cavity 115 is defined internally by collar 114 and externally by a proximal cylindrical wall segment 109 and distal cylindrical wall segment 104. Catheter advancer 30 preferably interfaces with only one cylindrical wall segment to reduce friction: either collar 114 internally or walls 104 and 109 externally. Proximal cylindrical wall segment 109 may be fully cylindrical, but is preferably partially cylindrical and is linked with bridge 113 for structural support to prevent a user squeezing on grips 101 to deform base 10 such that rotation or translation of any components becomes more difficult or impeded. Distal wall segment 104 is preferably open along the top side where user controls on catheter advancer 30 are preferably located, as will be described. Base 10 is preferably transparent for ease of visualization of blood flashback into the flash chamber 64 of needle hub 70, and/or may be formed with a window 117 to reduce the amount of transparent material the user must look through to see blood in flash chamber 64 within needle hub 70.

Figures 4, 5:
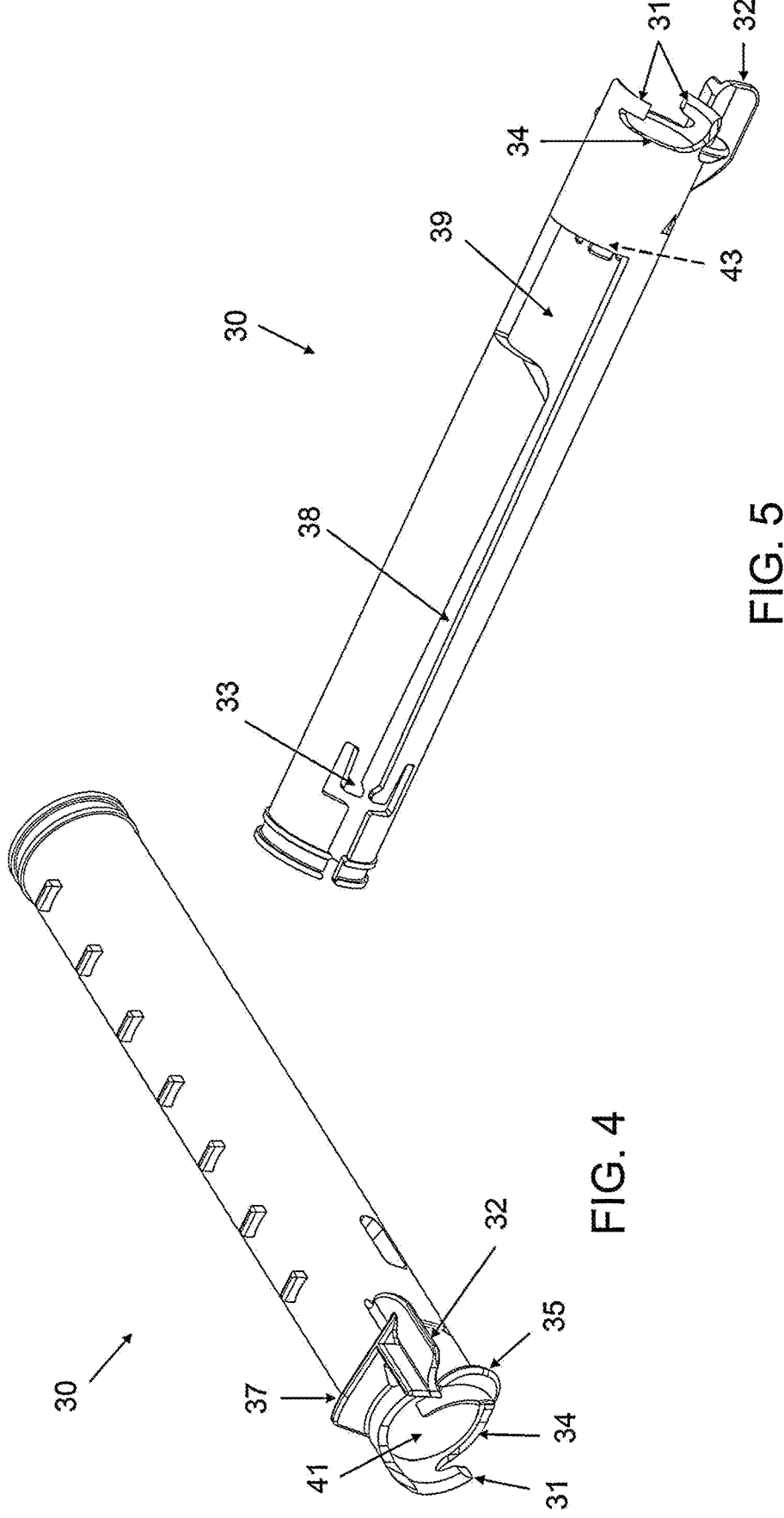
FIG. 4 is a side perspective view of the catheter advancer 30 of FIGS. 1-2.
FIG. 5 is another side perspective view of the catheter advancer 30 of FIG. 4.

As best seen in FIGS. 4-5 user controls of catheter advancer 30 include index finger rest 35, rotation tab 32, and advancement tab 37. Finger rest 35 preferably extends radially above the cylindrical body of catheter advancer 30, is generally positioned at a fixed lengthwise location, and has some lateral or angular width. The finger rest 35 preferably extends only a short height radially above the cylindrical body so that the user does not confuse it for advancement tab 37, but rather uses it only for enhanced user grip and control during early stages of the access procedure. Rotation tab 32 extends generally radially from the body of catheter advancer 30 generally at a fixed radial location and has a lengthwise span. Because rotation tab 32 needs to be easily moved by the user, the height that rotation tab 32 extends is preferably greater than that of finger rest 35. Advancement tab 37 generally extends radially over an angular span from the body of catheter advancer 30 and is generally located at a fixed lengthwise position. Because the user will push it for advancement of the catheter advancer 30, the radial extension of advancement tab 37 is preferably greater than finger rest 35.

Referring to FIGS. 1-2 and 4-5, catheter advancer 30 is a generally tubular structure formed with a helical face 34 at the distal end, and an elongate lengthwise slot 38 extending from the other end and toward helical face 34. The slot 38 extends distally to and opens into a transverse slot 39 offset proximally from helical face 34. The elongate strut 116 of base 10 may be positioned within either the elongate slot 38 or transverse slot 39. When elongate strut 116 of base 10 is within transverse slot 39, catheter advancer 30 can rotate relative to base 10 about axis 112 through an angular range defined by the extent of transverse slot 39, but cannot translate in any direction. The elongate slot 38 communicates with the transverse slot 39 along one common continuous side. Once catheter advancer 30 has been fully rotated such that elongate strut 116 of base 10 aligns with elongate slot 38, catheter advancer 30 becomes free to translate distally from this position, during which rotation about axis 112 is not possible. Elongate strut 116 of base 10 within elongate slot 38 acts as a linear guide for translation of catheter advancer 30 relative to base 10. Once catheter advancer 30 has translated distally from the starting position along elongate slot 38, it can be proximally translated back to the starting position without constraint, though this is not part of the preferred use case. Note that in the preferred embodiment, the angular range of transverse slot 39 of catheter advancer 30 and the opening of partial cylindrical wall 104 of base 10 are generally the same.

Base 10 also includes a pair of opposing and distally-protruding guide members 106 that embrace finger interfaces 55 of catheter hub 52 of catheter assembly 50. Guide members 106 are offset from central axis 112 of base 10 and protrude parallel thereto. In an embodiment, guide members 106 are elongate flat members formed with inwardly-protruding guide rails 107 that extend medially lengthwise, guide rails 107 fitting into conforming linear slots 57 along finger interfaces 55 of catheter hub 52, thereby allowing linear translation of the catheter assembly 50 relative to the base 10 yet preventing rotation. One skilled in the art will appreciate that there are other expedient means for linear guidance besides linear guide rails 107 and/or slots 57, and the invention is not limited thereto. For example, the "T-slot" shape of guide members 106 and "U-channels" of finger interfaces 55 as pictured could be reversed, wherein the guide members formed a "U-channel" through which the "T-slot" of finger interfaces 55 was guided.

Figure 8:
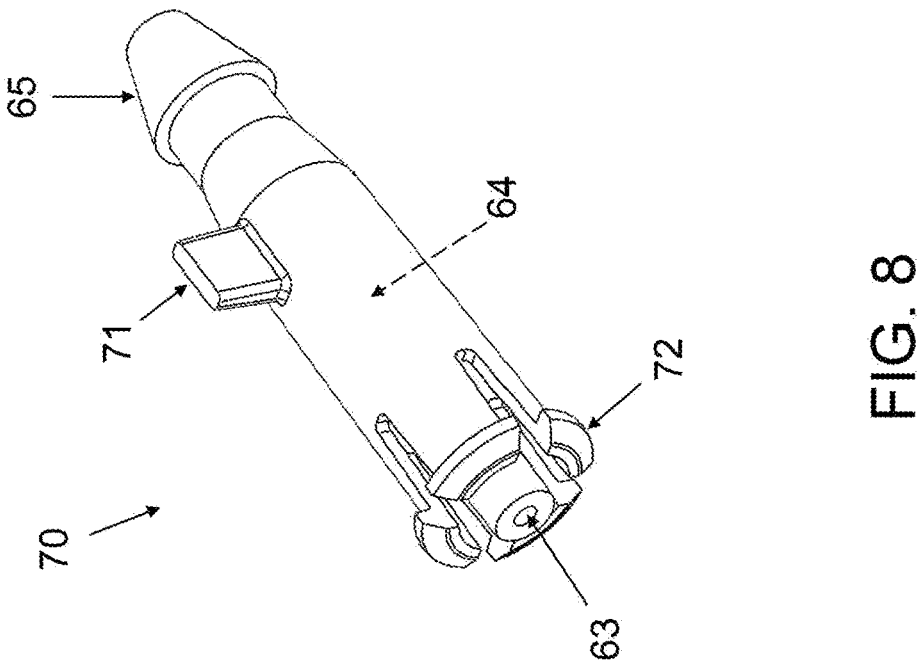
FIG. 8 is a side perspective view of the needle hub 70 of FIGS. 1-3.

As seen in FIGS. 2 and 8, needle hub 70 of needle assembly 60 is generally a tubular structure. At its distal end is needle mating hole 63 (see FIG. 8) in which the proximal end of needle 66 is housed and in fluid communication with internal flash chamber 64 of needle hub 70. In the preferred embodiment, the proximal end of needle hub 70 has a tubing barb 65 or other such fitting for mating with a flash extension tube 80 for the purpose of increasing the length and size of flash chamber 64. Alternatively, the proximal end 65 of needle hub 70 may simply be closed off or fitted with a vent membrane as would be obvious to those skilled in the art. Flash extension tube 80 is preferably a softer material than needle hub 70, though this is not required. The extension tube 80 itself is proximally terminated with a cap 81 which preferably contains a vent membrane of hydrophobic media across the cap to permit air but not blood to escape, as is commercially known. Extension tube 80 and cap 81 could likewise be formed together within the same invention, as well. Also at the distal end of needle hub 70 are flexing detent flanges 72 that allow simple assembly into inner cavity 118 of base 10, as needle hub is pushed distally through collar 114 until it snaps into place with flanges 72. Guide tab 71 extends radially/laterally from the body of needle hub 70 and its distal face abuts the proximal face of collar 114 of base 10 when needle hub 70 is fully seated in the assembly. In this way, flanges 72 and guide tab 71 constrain needle hub 70 from translating relative to base 10. However, needle hub 70 is free to rotate about axis 112 within collar 114 of base 10.

With needle 66 being fixed to needle hub 70, typically with an adhesive, weld, or other means, this implies that needle 66, as well as all of needle assembly 60, is free to rotate but not translate relative to base 10. As will be described, interactions between needle hub 70 and catheter advancer 30 prevent truly free rotation of needle assembly 60 and constrain such rotation to match that of catheter advancer 30 as defined by transverse slot 39 in the preferred embodiment and is ultimately controlled by the user via rotation tab 32. While the preferred embodiment allows needle 66 to rotate relative to base 10, this is not meant to be limiting. All other safety features activated by the rotational and translational engagements between base 10 and catheter advancer 30 are possible whether needle hub 70 rotates or not.

In an alternate embodiment the needle hub 70 may be a part of base 10, wherein collar 114 forms the outside of flash chamber 64 (i.e., cavity 118 becomes the flash chamber), the distal end of collar 114 is closed off with a needle hole 63, and the proximal end of collar 114 has means for attaching an extension tube or terminates the flash chamber, preferably with a vent membrane.

Figure 9:
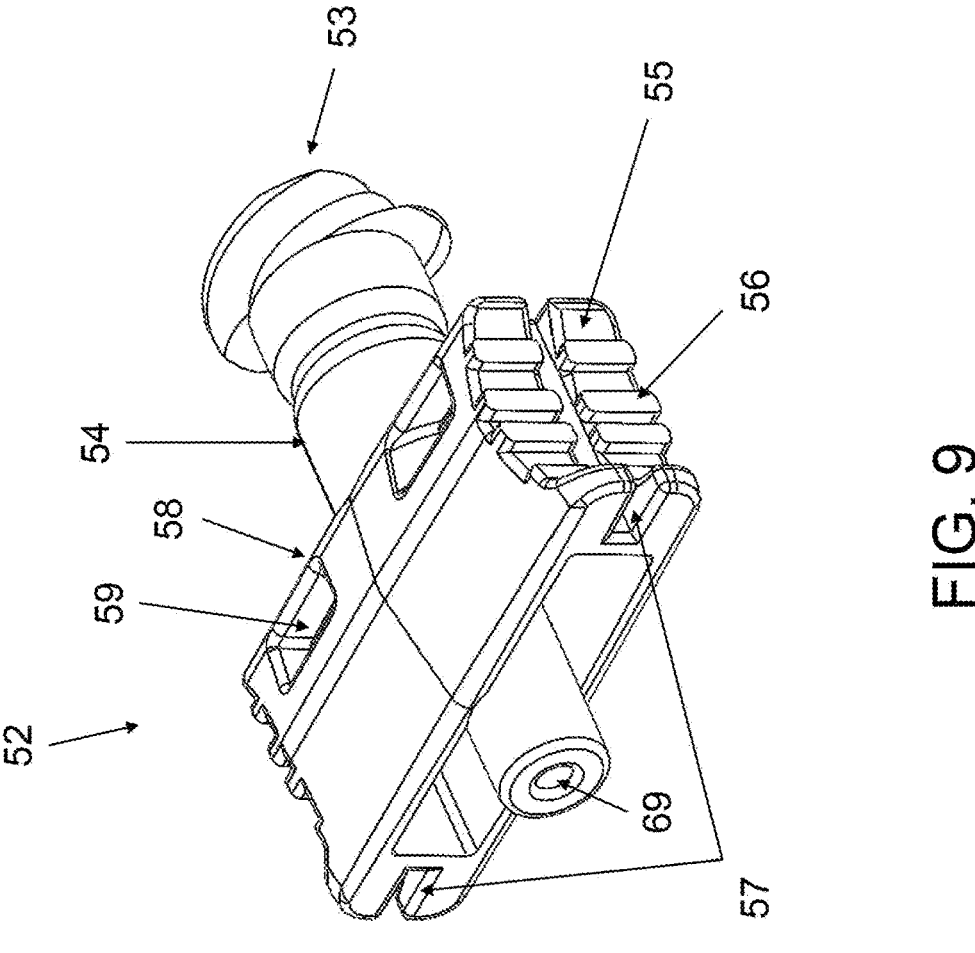
FIG. 9 is a side perspective view of the catheter hub 52 of FIGS. 1-3.

As seen in FIG. 9, catheter hub 52 of catheter assembly 50 additionally has a distal extension along axis 112 with catheter hole 69 into which the proximal end of catheter 51 is placed. A generally cylindrical extension 54 extends in the opposite direction along axis 112 from grips 55 and terminates proximally with luer lock threads 53. The interior of proximal extension 54 can be open or fitted with any variety of valves as known to those skilled in the art without departing from the invention. Proximal extension 54 extends along axis 112 from the back wall of grips 55, which serves as bearing surface 58. Bearing surface 58 interfaces with helical face 34 on the distal end of catheter advancer 30 during activation of the safety features of the present invention. Distal to bearing surface 58 may also be cavities 59 for locking engagement with distal hooks 31 of catheter advancer 30.

Base 10 mechanically engages catheter advancer 30, needle hub 70, and catheter hub 52, while catheter advancer 30 additionally engages both needle hub 70 and catheter hub 52, in the preferred embodiment. Catheter advancer 30 may be rotated via tab 32, and such rotation is delimited by travel of the tab 32 within the open section of cylindrical wall 104. Thus, user-driven rotation of catheter advancer 30 within base 10 linearly advances (i.e., distally translates) the entire catheter assembly 50 inclusive of proximal catheter hub 52 and catheter 51 relative to base 10 and catheter advancer 30, effectively translating the predetermined range of movement of catheter advancer 30 within base 10 into a predetermined initial safety advancement of the catheter assembly 50 over the incising end of the needle 66. This predetermined initial 'safety advancement' length is consistent and precisely controlled to sheath the beveled tip of the needle 66. More specifically, as seen in the inset of FIG. 1 the predetermined length $L_{SAFETY}$ equals the sum of the trim length $L_T$ plus the bevel length $L_B$ plus a nominal additional distance $L_N$ within a range of from 1% to 40% of $L_T+L_B$. The trim length TL is defined as the length between the distal tip of the catheter 50 and the proximal start of the needle bevel at the tip 62, and the bevel length $L_B$ is defined as the axial length of the needle bevel at the tip 62. The exact safety advancement length $L_{SAFETY}$ may depend somewhat upon other factors such as needle bore, but for most existing needles the additional distance $L_N$ will be within a range of from 1 mm-3 mm. This way, when performing the initial advancement action, the catheter 50 will be advanced just far enough to fully sheath the needle bevel but not so far as to risk shearing/cutting into the catheter 50, which can occur if the catheter tip is extended beyond the needle bevel tip by a large amount. The catheter tip is more flexible than the needle tip and if it hits a structure that causes it to bend the needle tip may puncture the catheter. The predetermined safety advancement length $L_{SAFETY}$ is always limited to the pre-specified distance to avoid this. After this safety advancement sheathing action is complete all other advancement of the catheter 51 over the needle tip 62 and into the patient's vessel, e.g., the 'threading/deployment advancement', may be performed manually by the user as per conventional practice.

From the user perspective, rotation of catheter advancer 30 within base 10 vis-à-vis rotation tab 32 rotates the helical face 34 which is in contact with bearing surface 58 of catheter assembly 50. Rotation of the helical face 34 counter-clockwise incrementally pushes the catheter assembly 50, inclusive of proximal hub 52 and catheter needle 51, until the distal tip of catheter 51 completely covers/sheaths the distal tip of needle 62 of needle assembly 60, thereby protecting the patient's vessel from potential trauma in the exemplary IV device. The foregoing advancement is accomplished with a unique rotation-to-linear translation mechanism in which rotation of the catheter advancer 30 is translated into linear advancement of catheter assembly 50 without rotation (the guide members 106 confining motion of the catheter assembly 50 relative to the base 10 to linear translation).

While the preferred embodiment allows only distal advancement of catheter assembly 50 relative to needle tip 62, an alternate embodiment may allow reversible translation of catheter assembly 50. In this embodiment, rotation in one direction (e.g., counterclockwise) will distally translate catheter assembly 50 such that the needle tip 62 is sheathed, while rotation in the opposite direction (e.g., clockwise) will proximally translate catheter assembly 50 such that needle tip 62 is exposed, which may be useful in some scenarios.

As seen in FIGS. 2 and 6-7, the generally cylindrical body of catheter advancer 30 is received within and rotates/slides within a conforming channel 115 in base 10, about/along axis 112. The channel 115 in base 10 is open along a section of its length defined by partial cylindrical wall 104. The cross-sectional shape of catheter advancer 30 is cylindrical, and a radially-extending advancement tab 37 protrudes from one end of the catheter advancer 30 at a distinctly different angular position from the rotation tab 32 outward through the opening in wall 104 and is configured to be pushed by the user (e.g., index finger) to advance the catheter assembly 50 into the patient's vessel. The advancement tab 37 may also be angled or curved for ergonomics and to prevent the user's finger from slipping off. Textures, protrusions, indentations and the like may also be used on advancement tab 37 without changing the invention. The two circumferential ends of the opening in partial cylindrical wall 104 of base 10 provide a stop for rotation tab 32, limiting rotation to a predetermined angle within a range of generally 80-130 degrees.

Figure 12:
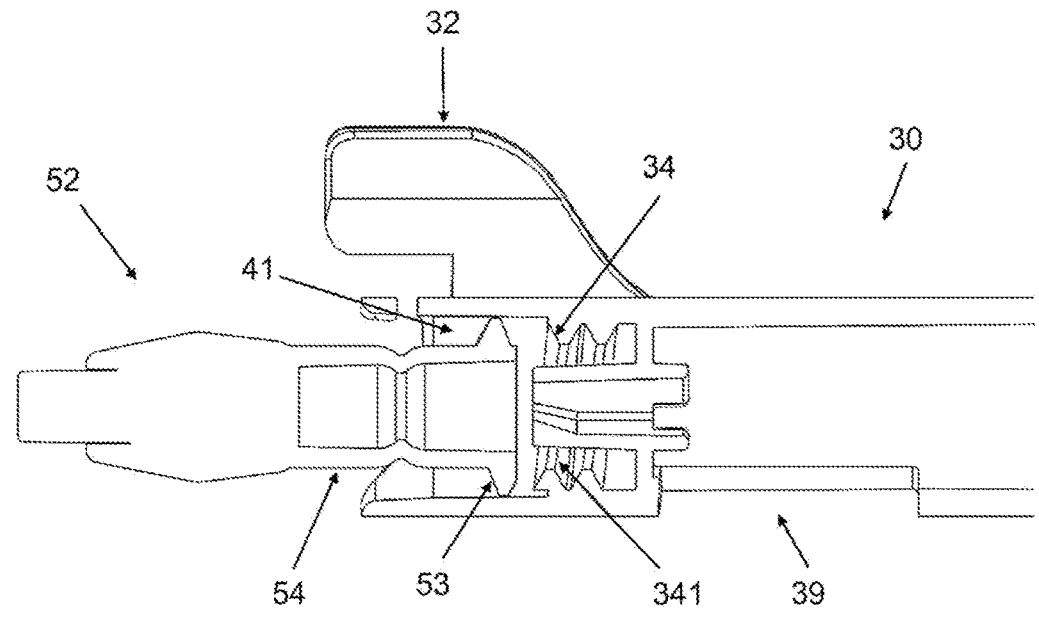
FIG. 12 is a partial cross sectional side view of catheter advancer 30 and catheter hub 52 according to an alternate embodiment.

The mechanism for translating rotation of the catheter advancer 30 within base 10 into linear translation of catheter assembly 50 further comprises a helical face 34 that engages the proximal hub 52 of catheter assembly 50 via bearing surface 58. The helical face 34 causes the cylindrical catheter advancer 30 to effectively vary in length with rotation angle along central axis 112, relative to base 10. At the starting angular position of catheter advancer 30, proximal hub 52 of catheter assembly 50 is engaged with a proximal point along helical face 34. Rotation of catheter advancer 30 within base 10 vis-à-vis rotation tab 32 slides helical face 34 to a more distal point along helical face 34 to push against bearing surface 58 of catheter assembly 50 until the catheter 51 completely covers the tip 62 of needle assembly 60, thereby sheathing it. In this way the angle of helical faces 34 can be designed given the length or angle of the bevel at needle tip 62 to ensure that protective sheathing is accomplished. In the alternate embodiment mentioned above, rotation of catheter advancer 30 in the opposite direction vis-à-vis advancer tab 32 unscrews a second helical face 341, similar but opposing the helical faces 34, backward from the catheter assembly 50 until the catheter needle 51 retracts the catheter assembly 50 and exposes the tip 62 of needle assembly 60 as seen in FIG. 1. Such an embodiment is illustrated in FIG. 12 where the helical faces are internal to cavity 41 of catheter advancer 30 and the luer lock threads 53 are used in place of bearing surface 58. Here helical face 34 pushes catheter hub 52 in the distal direction through contact with the proximal face of luer threads 53, and helical face 341 pulls catheter hub 52 back in the proximal direction through contact with the distal face of luer threads 53.

In the preferred embodiment, helical face 34 is delimited with one or more abutments (i.e., transverse or lateral interfaces) to engage the bearing surface 58 of catheter hub 52 at the end of catheter advancer 30 rotation. In the illustrated embodiment the abutments are provided by hooks 31 on catheter advancer 30 described below. These interface (s) or abutment(s) provide a solid pushing contact on bearing surface 58 that is impossible to back-drive or reverse rotation of catheter advancer 30 in a manner that would re-expose needle tip 62 and potentially cause vessel trauma. Hence, the final degrees of rotation of catheter advancer 30, within the aforementioned angular range, preferably provide an effective lock on the distal position of catheter 51 sheathing needle tip 62. To make this obvious to a user (i.e., completion of rotation and needle sheathing locked), features may be included on base 10 and catheter advancer 30 that provide tactile feedback, such as a click, that can be felt by the user. For example, protuberance 119 on the distal face of base 10 (see FIGS. 6-7) can slip over protuberance 42 on catheter advancer 30 (see FIG. 2) to provide such a "click" feel, though the invention is not limited to only this type or location of engagement, as would be obvious to those skilled in the art. The amount of such engagement can also be varied to produce the desire effect within the invention.

One skilled in the art will readily understand that the mechanism for linear translation of catheter assembly 50 may take other forms, such as push-to-advance, or may be automated or semi-automated such as spring-advance, etc. For example, it is envisioned that the pressure of the blood flashback may contribute hydraulically to mechanically push the catheter forward by the fixed amount $T_{SAFETY}$. In addition, initiation of linear translation may be triggered. For example, triggered advancement may be initiated by a change in force exerted on the needle 60 as the tip 62 enters the body structure of interest. In another embodiment, triggered advancement may be initiated by the flow of fluid (e.g., blood) into the needle tip 62. For example, the pressure/flow from blood flashback may trip a release latch allowing a mechanical spring to move the catheter forward $T_{SAFETY}$. Alternatively, the force of pushing the needle tip 62 through tissue may toggle release a spring mechanism similar to a push-detent pen, such that as soon as this initial reaction force ends, the catheter springs forward by fixed amount $T_{SAFETY}$.

One skilled in the art will understand that a variety of suitable mechanisms may trigger catheter advancement and linearly translate catheter assembly 50, including but not limited to a lever, linkage, screw, gear, cam, or hydraulic mechanism. The triggering/advancement may also rely on the release of stored mechanical energy to affect catheter advancement, such as but not limited to the release of a compressed spring. In addition, a mechanism is provided for translationally locking catheter advancer 30 to base 10 when device 1 is in the starting position pictured in FIG. 1. As best seen in FIG. 6, base 10 has a distal wall 111, behind which is a locking slot 108. When needle tip 62 is exposed and device 1 is ready to puncture a patient's tissue (i.e., prior to any rotation of catheter advancer 30), advancement tab 37 of catheter advancer is seated within locking slot 108. This way, any distal force on catheter advancer 30 does not cause any distal advancement of catheter advancer 30 because advancement tab 37 abuts the proximal face of wall 111 and cannot move translationally relative to base 10. It is not until after catheter advancer 30 has been fully rotated to the sheathed needle tip position that advancement tab 37 is fully out of the locking slot 108 such that catheter advancement can begin. That is, the prominent push tab for catheter advancement (advancement tab 37) is not fully visible or accessible to the user until after the safety features have been engaged and needle tip 62 is sheathed by catheter 51 and locked in this position. This is the point at which elongate strut 116 of base 10 aligned with linear channel 38 of catheter advancer 30.

Additionally, the device 1 provides a means of locking catheter assembly 50 to catheter advancer 30. When in the starting position pictured in FIG. 1 where needle tip 62 is exposed and ready to puncture a patient's tissue, bearing surface 58 of catheter hub 52 is seated in its proximal-most position relative to helical faces 34 of catheter advancer 30. In this position, hooks 31 of catheter advancer 30 are inserted into locking cavities 59 of catheter hub 52 such that the two parts cannot be separated until catheter advancer 30 is rotated to the safe position and hooks 31 are removed from cavities 59. Recall that guide rails 107 of base 10 prevent relative rotation of catheter hub 52 through engagement with slots 57 in this position, so catheter hub 52 cannot itself be rotated out of the locked position either. This, together with the translational lock of catheter advancer 30 to base 10 mentioned above, prevents unintended movement of catheter 51 distal to needle tip 62, which could cause catheter shearing.

The needle assembly 60 comprises an elongate stainless-steel needle 66 with distal beveled tip 62, mounted on a transparent plastic hub 70 that displays a flash chamber 64. Successful vein entry is indicated when the flash chamber 64 fills with blood. Note that needle 66 may also have a hole somewhere along its length to allow blood to fill the space between the needle and catheter thereby showing flashback earlier (before it reaches the flash chamber), as is commonly known to those skilled in the art, without departing from the invention. The needle hub 70 is inserted into collar 114 of base 10 from the proximal side until flexing flanges 72 snap back open and guide tab 71 abuts the proximal face of collar 114. As noted, needle hub 70 is free to rotate within collar 114 at this point, as well as needle assembly 60 about axis 112. To assemble catheter advancer 30 with the already-assembled needle assembly 60 and base 10, needle hub 70 is first rotated until guide tab 71 is aligned with elongate strut 116 of base 10. Then elongate slot 38 of catheter advancer 30 is aligned with elongate strut 116 about axis 112, the proximal opening of elongate slot 38 is spread open enough such that detent prongs 33 straddle elongate strut 116, and catheter advancer is pushed in the proximal direction until inner wall 43 of catheter advancer 30 abuts the distal face of needle hub 70. At this point, rotation tab 32 of catheter advancer 30 is in the safe position and must be rotated to the starting position. Also in this position, elongate strut 116 is aligned with transverse slot 39 of catheter advancer 30 and guide tab 71 of needle hub 70 is in elongate slot 38 of catheter advancer 30. Hence, needle assembly 60 is rotatably linked to catheter advancer 30 and any rotation of catheter advancer 30 will also rotate needle assembly 60. Catheter assembly 50 is then aligned with axis 112, where slots 57 of catheter hub 52 are aligned with guide rails 107 of base 10, and pushed in the proximal direction until bearing surface 58 abuts helical faces 34 of catheter advancer 30. In this position, proximal extension 54 and luer lock threads 53 are seated in distal cavity 41 of catheter advancer 30, but catheter assembly 50 is not yet locked to catheter advancer 30. To complete the assembly, proximally directed force is applied to catheter hub 52 while catheter advancer 30 is rotated to the starting position, and in so doing, hooks 31 of catheter advancer 30 engage with cavities 59 of catheter hub 52, thereby locking catheter assembly 50 to catheter advancer 30, and advancement tab 37 of catheter advancer 30 is moved into slot 108 of base 10, thereby translationally locking catheter advancer 30 to base 10. The needle tip 62 is exposed with the bevel up in this starting position and device 1 is ready for use.

Referring to FIG. 5 it can be seen that the catheter advancer 30 is formed with a pair of detent prongs 33 inwardly offset from the distal end of slot 38. The detent prongs 33 are located on opposing sides of the slot 38 and face each other, providing a momentary constriction to the width of the slot 38 that can be overcome. The guide tab 71 extending from the needle hub 70 interfaces with the catheter advancer 30 by insertion into the elongate slot 38 such that the two components rotate together. After catheter advancer 30 has been rotated to the safe position, guide tab 71 of needle hub 70 is aligned with elongate strut 116 of base 10, both of which slide within elongate slot 38 in the catheter advancer 30 as catheter 51 is advanced into the patient. As catheter 51 is advanced over needle 66 into the patient and approaches full insertion, detent prongs 33 of catheter advancer 30 come into contact with guide tab 71 of needle hub 70, which is aligned with elongate strut 116 of base 10, and provide a slight change in advancement resistance that can be felt by the user as detect prongs 33 are bent open. This tells the user that full advancement is nearly complete. Then continued distal advancement of catheter advancer 30 produces a noticeable click as the stored energy from bending detect prongs 33 open is released when they reach gap 121 in elongate strut 116 of base 10. This snapping back together of detent prongs 33 provides tactile feedback to the user that advancement of the catheter is complete and that needle 66 is fully secured within catheter advancer 30 for post-procedure needle stick safety.

In operation, from the "starting" configuration of FIG. 1, the exemplary intravenous device 1 has the tip of needle 62 exposed distal to the tip of catheter 51 in order to puncture a patient's tissue and vessel. In this embodiment, pre-mature movement of catheter advancer 30 is prevented as an operational safety feature to prevent possible shearing of catheter 51 prior to gaining intravenous access by hooks 31 of catheter advancer 30 engaging cavities 59 of catheter hub 52. Movement by means of slidable translation of catheter advancer 30 relative to base 10 is prevented by advancement tab 37 of catheter advancer 30 being locked within slot 108 of base 10. This effectively governs extension of the distal tip of catheter 51 and locks it in the proximal-most position after the exact safety advancement length $L_{SAFETY}$. Other means of translational locking are also provided by interference between the proximal edge of transverse slot 39 and the proximal edge of elongate strut 116 of base 10.

After successful vessel puncture is complete blood flashback will be visible in flash chamber 64 of needle hub 70. In the embodiment where there is an extended flash chamber, e.g., via extension flash tube 80, blood will continue to fill the chamber as long as needle tip 62 and distal tip of catheter 51 remain inside the vessel. However, if either distal tip exits the vessel, the filling of the flash chamber 64 and/or the extension flash tube 80 will stop, giving a visual indication to the user that the needle tip is no longer in the vessel. Having the extended flash chamber (FIG. 3) thereby provides a longer time over which the user has visual feedback on the internal placement of the distal needle and catheter tips.

The rotation tab 32 of catheter advancer 30 is rotated counter-clockwise from the user's perspective after visualizing blood flashback in chamber 64, serving five safety purposes in the preferred embodiment, though any such subset of purposes could be enabled in an alternate embodiment within the same invention: 1) it slightly advances catheter assembly 50 relative to catheter advancer 30, base 10, and needle assembly 60 such that the distal tip of catheter 51 is positioned distal to needle tip 62 thereby sheathing the needle tip 62 to provide protection against vessel trauma due to the needle; 2) it mechanically blocks catheter assembly 50 from moving proximally relative to the sheathed position by the flat ends of helical faces 34 of catheter advancer 30 abutting bearing surface 58 of catheter hub 52 thereby preventing the possibility of re-exposing needle tip 62 during the catheter advancement process and potentially causing vessel trauma; 3) it unlocks advancement tab 37 from within a slot 108 in base 10 thereby freeing catheter advancer 30 from its translational lock and allowing linear movement to advance the catheter; 4) it unlocks catheter assembly 50 from catheter advancer 30 by removing hooks 31 from cavities 59 thereby allowing free release of device 1 from the inserted catheter; and 5) it makes the beveled tip of needle 62 rotate such that the point of the needle tip 62 is farther away from the back wall of the vessel thereby further reducing the possibility of vessel trauma due to needle tip 62. The safety purposes are enabled through said rotation as helical faces 34 of catheter advancer 30 bear against bearing surface 58 of catheter hub 52 of catheter assembly 50 and force distal advancement of catheter assembly 50 and hence the catheter 51 to sheath needle tip 62. Now needle tip 62 is prevented from extending distally beyond the sheathed catheter 51. In addition, base 10 prevents catheter advancer 30 from rotating back once advancement of catheter assembly 50 has begun because elongate strut 116 of base 10 and guide tab 71 of needle hub 70 are captured in elongate slot 38 of catheter advancer 30. The catheter assembly 50 remains held in base 10. The advancement tab 37 of catheter advancer 30, previously hidden in base 10 and locking catheter advancer 30 to base 10, now rotates to the top position. The push tab 37 is now visible and accessible to the user in the opening of partial cylindrical wall 104 of base 10. The catheter advancer 30 can now be pushed distally by the user to fully advance the catheter assembly 50 and secure the needle 66.

Thus, rotation of catheter advancer 30 by rotation tab 32 accomplishes a controlled procedure:

Catheter assembly 50 is advanced to sheath needle tip 62;

Catheter assembly 50 is prevented from retracting to re-expose the needle tip 62;

Catheter advancer 30 is unlocked from base 10 for translational movement along center axis 112;

Catheter assembly 50 is unlocked from catheter advancer 30;

Needle assembly 60 is rotated so that the incising portion of the beveled needle tip 62 is moved away from the vessel back wall;

At full advancement, the catheter assembly 50 has been carried distally on the forwardly-protruding guide rails 107 of base 10 that linearly guide slots 57 of catheter hub 52 and beyond, and the contoured finger interfaces 55 are exposed, can be gripped and secured by the user, and base 10 removed from fully inserted catheter assembly 50 at the procedure site with the needle 66 secured within catheter advancer 30 which is now locked in the forward position for needle security. When seated in the patient's vessel and the remainder of the device 1 has been removed from catheter assembly 50, securement of the catheter can be completed. Finger interfaces 55 and the wide hub 52 facilitate such securement by providing sturdy backing and grip for screwing other devices onto luer lock threads 53.

Figure 10:
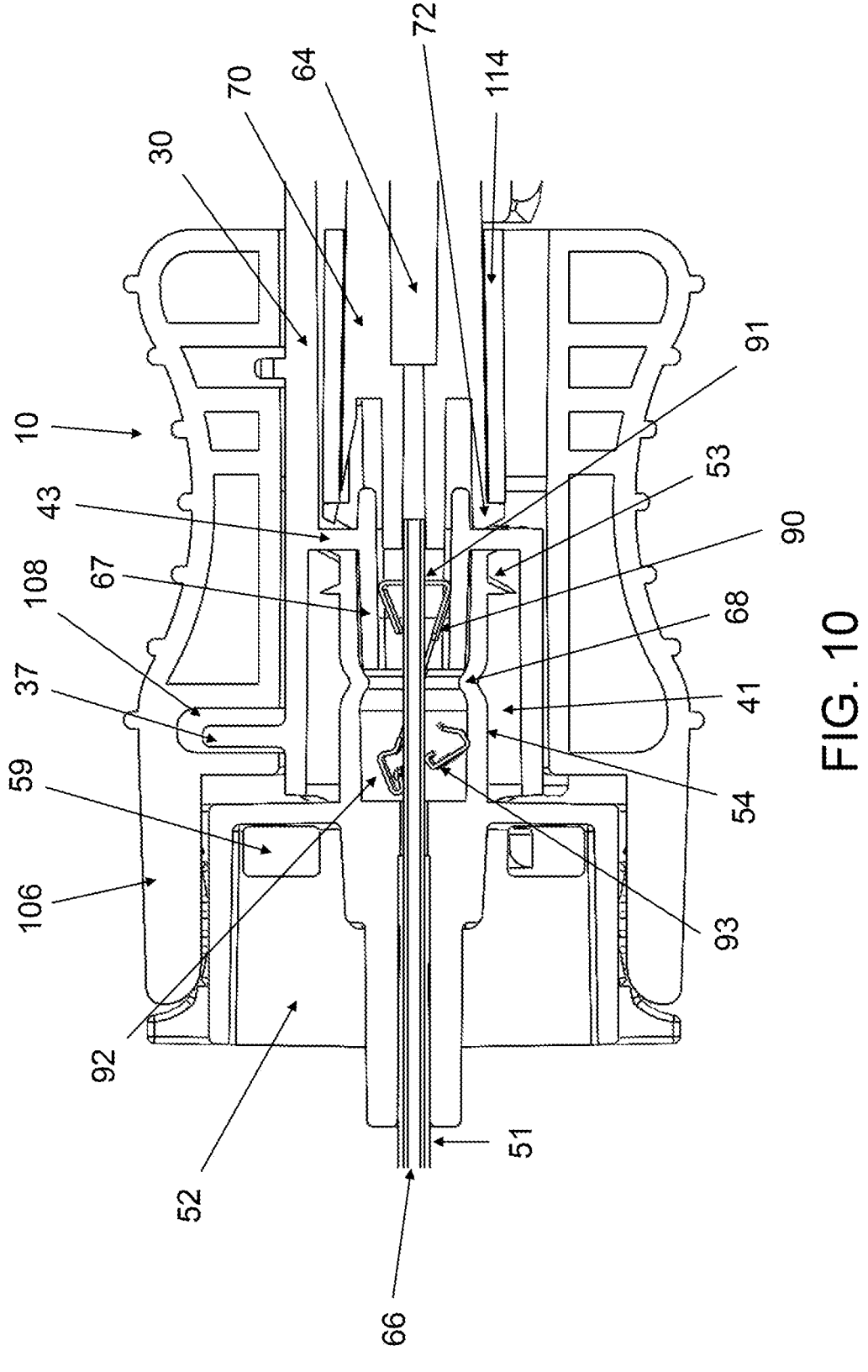
FIG. 10 is a partial, top cross-sectional view of intravenous device 1 zoomed in over the base 10 of FIGS. 1-3.

While the preferred method of catheter advancement, as described, is pushing distally on advancement tab 37 of catheter advancer 30 with the index finger, this one-handed method is not the only possibility with the present invention. There may be clinical scenarios where a two-handed advancement method is preferred, wherein the user stabilizes his/her grip on base 10 with one hand and then uses his/her other hand to pull catheter assembly 50 along the distally inserted needle 66. In this scenario, the user preferably pulls catheter assembly 50 from the wide grips 55 between their thumb and middle/index finger. In this two-handed pull method, catheter advancer 30 still moves distally together with catheter assembly 50 for the full insertion and detent prongs 33 click into place in gap 121 of elongate strut 116 of base 10, thereby providing needle-stick protection. As seen in FIG. 10, this is enabled by a spring clip 90 that is housed inside proximal extension 54 of catheter hub 52. Needle 66 passes through a hole 91 in the proximal wall of spring clip 90 and holds the two distal spring clip ends 92 and 93 open while needle 66 remains in catheter assembly 50. The distal opening of spring clip 90 by needle 66, which stored energy in spring clip 90, allows an interference fit between at least one of distal spring clip ends 92 or 93 and inner detent 68 of proximal extension 54 of catheter hub 52. At the other end, the proximal wall of spring clip 90 is more securely snapped into distal extension 67, centered around axis 112 within distal cavity 41 of catheter advancer 30, such that it cannot be removed under forces typically applied during intravenous catheterization. An adhesive may be applied to increase the holding force between the proximal wall of spring clip 90 and distal extension 67 of catheter advancer 30. In this way, distal pulling of catheter hub 52 also pulls catheter advancer 30 until distal tip 62 of needle 66 passes proximally through ends 92 and 93 of spring clip 90, which then releases its stored energy and closes over needle tip 62. The dimensions of catheter advancer 30 are such that this closing of spring clip 90 over needle tip 62 occurs when detent prongs 33 click into gap 121. Hence, needle tip 62 is covered by spring clip 90 and the entire needle 66 is encompassed by catheter advancer 30.

Figure 11:
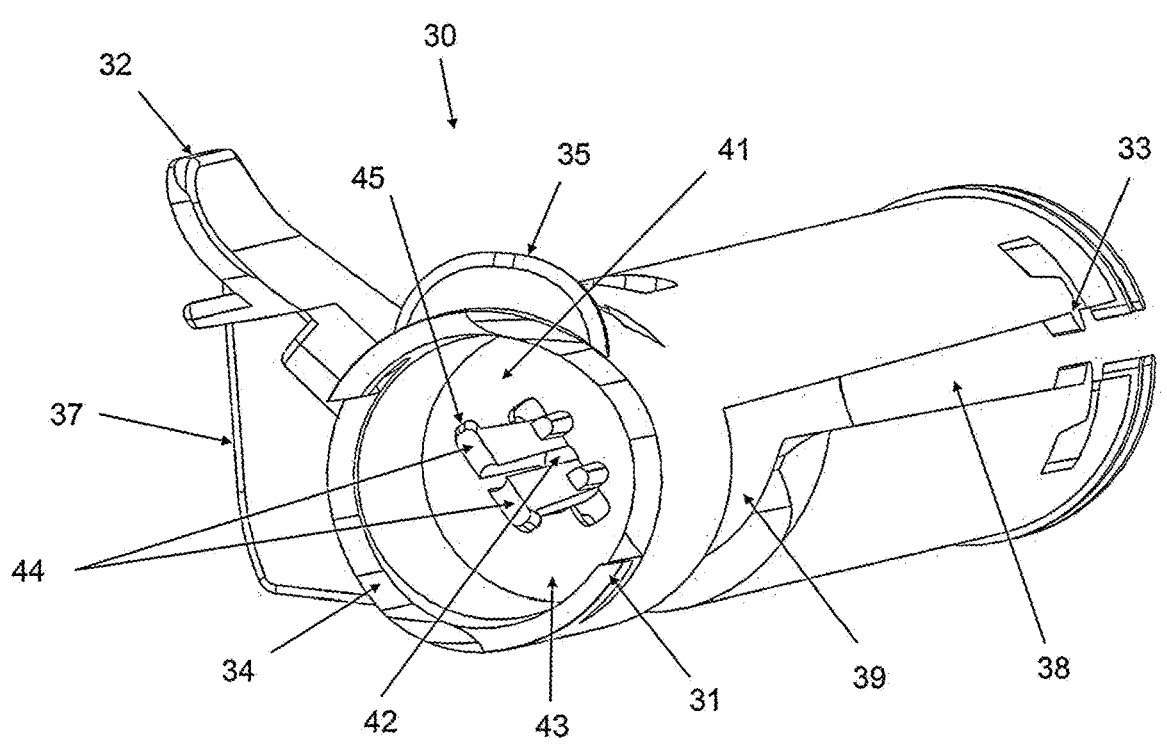
FIG. 11 is a front perspective view of an alternate embodiment of the catheter advancer 30 of FIGS. 1-3.

In the alternate embodiment shown in FIG. 11, spring clip 90 is replaced with spring legs 44, which are themselves distal extensions from wall 43 within cavity 41 of catheter advancer 30. At least two spring legs 44 are positioned around needle hole 42, which is aligned with axis 112 and allows free passage of needle 66. Spring legs 44 have radially extending feet 45 on their distal ends that engage inner detent 68 of proximal extension 54 of catheter hub 52 in the same way that distal spring clip ends 92 and 93 did in the former embodiment. When needle 66 is present, feet 45 interfere with inner detent 68, but after needle 66 is removed, spring legs 44 can flex medially such that feet 45 no longer engage inner detent 68 and the rest of device 1 is freely removed from fully inserted catheter assembly 50. Note that all other safety features of device 1 listed above are unaffected by whether spring clip 90 is used or spring legs 44 are used to enable needle securement from a two-handed advancement method.

It should now be apparent that the foregoing provides an easy-to-use access device that is designed to facilitate and enhance safety of insertion of the needle and advancement of the catheter for the exemplary IV device. The device enables greater control and safety in the needle/catheter assembly for approach and advancement, facilitates small movements of the needle/catheter or either part individually, and prevents unwanted movement, all without interrupting the flow of the IV start procedure. This facilitates more efficient IV placement and success rates, and decreases vessel trauma, IV failure, and patient discomfort.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

We claim:

1. A device for inserting a catheter, comprising:
a base configured to be gripped by a user;
a needle extending along an axis from a needle hub to a distal incising end with a beveled tip;
a catheter extending along said axis from a hub to a distal end and slidably translatable over said needle; and
a catheter advancer rotatably seated in said base and constrained thereby to a predetermined range of rotational movement around said axis, the catheter advancer being engageable with said catheter and configured to translate said range of rotational movement into a predetermined initial safety advancement of said catheter linearly along said axis and relative to said base and said catheter advancer to a fixed distal position ensheathing the incising end of said needle, wherein the catheter advancer remains entirely proximal of the distal tip of said needle during the predetermined initial safety advancement.

2. The device for inserting a catheter according to claim 1, wherein said initial safety advancement advances said catheter to a distal position that sheaths the beveled tip of said needle.

3. The device for inserting a catheter according to claim 2, wherein said catheter advancer is configured to selectively lock said catheter in a proximal-most position.

4. The device for inserting a catheter according to claim 3, wherein said catheter advancer is configured to selectively unlock said catheter to allow slidable translation of said catheter along said axis.

5. The device for inserting a catheter according to claim 2, wherein said catheter advancer is configured to mechanically prevent the beveled tip of said needle from being unsheathed once said initial safety advancement has been completed.

6. The device for inserting a catheter according to claim 1, wherein said catheter advancer is configured to engage said needle hub and rotate said needle about said axis relative to said base when said catheter advancer is moved within said predetermined range of movement.

7. The device for inserting a catheter according to claim 1, wherein said catheter advancer includes a distal finger tab projecting radially therefrom relative to said needle for finger-rotation of said catheter advancer within said base.

8. The device for inserting a catheter of claim 1 wherein the catheter advancer comprises helical threads for engagement with said catheter.

9. The device for inserting a catheter according to claim 1, wherein said base has at least one contoured finger grip.

10. The device for inserting a catheter according to claim 1, wherein said catheter advancer is configured to encompass said needle as said catheter advancer slidably translates.

11. A device for inserting a catheter, comprising:
   a base configured to be gripped by a user, said base defining a channel extending along an axis;
   a needle having a distal incising end and a proximal needle hub, the distal incising end having a beveled tip extending along a length $L_B$ of said axis;
   a catheter assembly comprising a proximal hub and a catheter that is slidably translatable over the incising end of said needle, thereby defining a trim length $L_T$ extending along said axis between a distal end of said catheter and a proximal end of said beveled tip of said needle;
   and
   a catheter advancer rotatably seated in said base, constrained therein to a predetermined range of rotational movement around said axis, and engageable with said catheter assembly and configured for translation of said range of rotational movement of said catheter advancer into linear movement of said catheter assembly in a distal direction along said axis by a predetermined length $L_{SAFETY}$ prior to threading said catheter into a patient, wherein $L_{SAFETY}$ is greater than or equal to a sum of $L_B$ plus $L_T$ plus a nominal distance $L_N$ within a range from 1.0% to 40% of $L_B$ plus $L_T$;
   wherein the catheter advancer remains entirely proximal of the distal incising end of said needle during translation of said catheter assembly along said axis by said predetermined length.

12. The device for inserting a catheter according to claim 11, wherein a safety advancement sheaths the distal incising end of said needle.

13. The device for inserting a catheter according to claim 11, wherein said catheter advancer is configured to selectively lock said catheter in a proximal-most position.

14. The device for inserting a catheter according to claim 13, wherein said catheter advancer is configured to selectively unlock said catheter to allow slidable translation of said catheter along said axis.

15. The device for inserting a catheter according to claim 11, wherein rotation of said catheter advancer rotates said needle about said axis relative to said catheter.

16. The device for inserting a catheter according to claim 11, wherein said catheter advancer is configured to mechanically prevent the beveled tip of said needle from being unsheathed once an initial safety advancement has been completed.

17. The device for inserting a catheter according to claim 11, wherein said catheter advancer includes a distal finger advancement tab projecting radially therefrom relative to said needle axis.

18. The device for inserting a catheter according to claim 11, wherein said base has at least one contoured finger grip.

19. The device for inserting a catheter according to claim 11, wherein said catheter advancer is configured to encompass said needle as said catheter advancer slidably translates.

* * * * *